United States Patent
Hoernig

(10) Patent No.: US 10,383,991 B2
(45) Date of Patent: Aug. 20, 2019

(54) DIALYZER

(71) Applicant: FRESENIUS MEDICAL CARE DEUTSCHLAND GMBH, Bad Homburg (DE)

(72) Inventor: Norbert Hoernig, Neiderwerrn (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 0 days.

(21) Appl. No.: 15/315,905

(22) PCT Filed: May 28, 2015

(86) PCT No.: PCT/EP2015/001093
§ 371 (c)(1),
(2) Date: Dec. 2, 2016

(87) PCT Pub. No.: WO2015/185197
PCT Pub. Date: Dec. 10, 2015

(65) Prior Publication Data
US 2017/0106131 A1    Apr. 20, 2017

(30) Foreign Application Priority Data

Jun. 4, 2014 (DE) .......... 10 2014 008 367

(51) Int. Cl.
| | |
|---|---|
| *A61M 1/28* | (2006.01) |
| *A61B 5/00* | (2006.01) |
| *A61B 5/021* | (2006.01) |
| *A61B 5/0225* | (2006.01) |
| *A61M 39/22* | (2006.01) |

(52) U.S. Cl.
CPC .......... *A61M 1/282* (2014.02); *A61B 5/0225* (2013.01); *A61B 5/02141* (2013.01); *A61B 5/6866* (2013.01); *A61M 1/28* (2013.01); *A61M 39/223* (2013.01); *A61M 2205/07* (2013.01);
(Continued)

(58) Field of Classification Search
CPC .......... A61M 1/282; A61M 2205/07; A61M 2205/50; A61M 2205/52; A61M 2230/30; A61M 39/223
See application file for complete search history.

(56) References Cited

U.S. PATENT DOCUMENTS

| | | | | |
|---|---|---|---|---|
| 4,883,462 A | * | 11/1989 | Williamson | A61H 9/0078 604/540 |
| 6,026,684 A | * | 2/2000 | Calder | A63B 21/028 73/379.02 |

(Continued)

FOREIGN PATENT DOCUMENTS

| | | |
|---|---|---|
| DE | 10224750 | 12/2003 |
| EP | 0790841 | 11/2000 |
| WO | WO 2013/051927 | 4/2013 |

*Primary Examiner* — Imani N Hayman
(74) *Attorney, Agent, or Firm* — Jacobson Holman, PLLC.

(57) ABSTRACT

The present invention relates to a dialyzer, in particular to a peritoneal dialyzer, comprising at least one compressor and comprising at least one pneumatic consumer which is in communication with the compressor such that it can be acted on by compressed air from the compressor, wherein the dialyzer communicates or can communicate with at least one blood pressure cuff such that the blood pressure cuff can be supplied with compressed air by the compressor of the dialyzer.

10 Claims, 1 Drawing Sheet

(52) U.S. Cl.
CPC ..... *A61M 2205/50* (2013.01); *A61M 2205/52* (2013.01); *A61M 2230/30* (2013.01)

(56) References Cited

U.S. PATENT DOCUMENTS

| | | |
|---|---|---|
| 9,999,560 B2 * | 6/2018 | Farese .................. A61H 9/0078 |
| 2001/0012917 A1 | 8/2001 | Inukai et al. |
| 2002/0193691 A1 | 12/2002 | Sato |
| 2003/0120170 A1 | 6/2003 | Zhu et al. |
| 2005/0234384 A1 | 10/2005 | Westberg et al. |

* cited by examiner

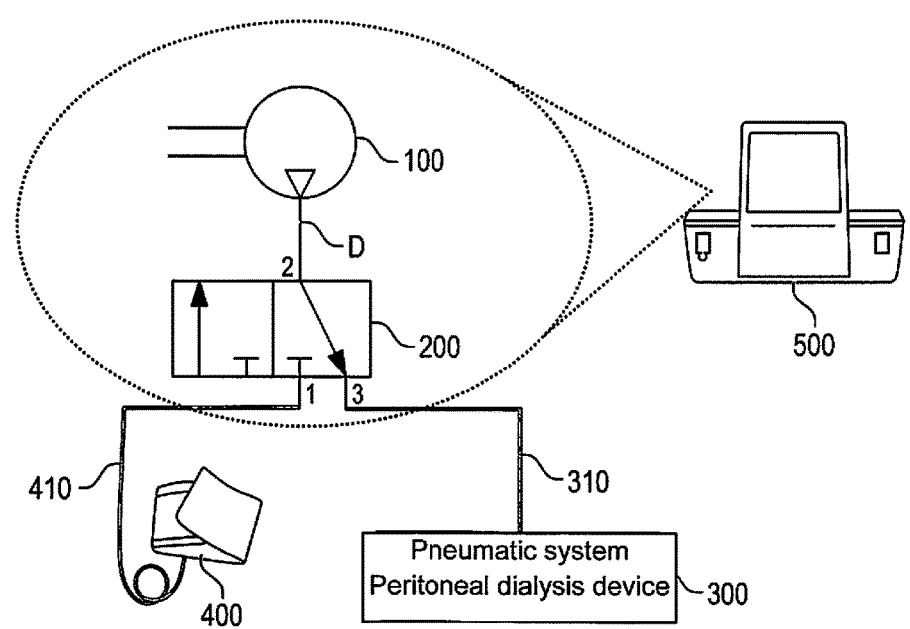

DIALYZER

The present invention relates to a dialyzer, in particular to a peritoneal dialyzer, comprising at least one compressor and comprising at least one pneumatic consumer which is in communication with the compressor such that it can be acted on by compressed air from the compressor.

Peritoneal dialyzers are known from the prior art which have a compressor which supplies a plurality of consumers with compressed air as required. Said consumers include, for example, pneumatic actuators in the form of pneumatic valves which control the flow paths in the disposable which is coupled to the peritoneal dialyzer during the treatment of the patient. Further examples for pneumatic actuators which can be supplied with compressed air from the compressor are bleed valves at the hydraulic pump which are required for the degasing of the hydraulic fluid and an air cushion beneath the drawer which severs the pressing of the disposable between the drawer and the machine block. The pneumatic pressure is typically restricted to a specific pressure value, e.g. 2 bar.

The control of the compressor takes place via an action computer.

An apparatus for determining body water is known from US 2003/0120170 A1 which is based on a resistance measurement. The blood pressure is maintained in a specific range during this body water determination. US 2001/0012917 A1 and US 2002/0193691 A1 describe the measurement of the blood pressure of a patient during a dialysis treatment.

It is the underlying object of the present invention to further develop a dialyzer, in particular a peritoneal dialyzer, such that the carrying out of the dialysis treatment is simplified.

This object is satisfied by a dialyzer having the features of claim 1. Provision is accordingly made that the dialyzer communicates or can communicate with at least one blood pressure cuff such that the blood pressure cuff can be supplied with compressed air by the compressor of the dialyzer. It is thus the underlying idea of the present invention to further develop a dialyzer of the initially named kind such that the compressor of the unit does not only serve for the supply of conventional pneumatic actuators, but also for the compressed air supply of a blood pressure cuff.

This has the advantage that the blood pressure measurement can be integrated directly into the dialyzer and that preferably no further separate unit is required which has additionally to be operated by the patient or by the user.

The term "compressor" is to be understood generally and does not only comprise a compressor in a narrower sense, but also any desired compressed air source.

In a preferred embodiment of the invention, all the components required for the blood pressure measurement and, optionally, for the processing of the measured data, are integrated into the dialyzer, with the exception of the blood pressure cuff.

In accordance with the invention, the compressor of the dialyzer thus does not only serve the supply of the consumers known from the prior art such as valves or the air cushion for fixing the disposable cassette, but also the compressed air supply of the blood pressure cuff. A separate compressor, air pump, etc., provided especially for the compressed air supply of the blood pressure cuff, is thus not required in accordance with the invention.

Provision is preferably made that the dialyzer has at least one connection to which the blood pressure cuff is or can be releasably connected. This connection can be a plug-in connection. This allows a particularly simple connection of the blood pressure cuff to the dialyzer.

Provision is made in a further embodiment of the invention that at least one valve is located between the compressor and the blood pressure cuff and that one or more lines, in particular the compressed air line between the compressor and the blood pressure cuff, can be closed off or released by means of said valve.

If no blood pressure measurement is required, the valve is preferably in the closed position, i.e. the pressure line between the pressure side of the compressor and the blood pressure cuff is blocked. If the blood pressure is to be measured, the valve is opened so that the blood pressure cuff can be supplied with compressed air from the compressor.

The valve is preferably configured as a multiway valve and preferably as a 2-way valve which is designed such that either the blood pressure cuff or one or more of the other consumers is/are in compressed air communication with the compressor.

In a further embodiment of the invention, the dialyzer has a control or regulation unit which is configured such that it controls or regulates the supply of the blood pressure cuff with compressed air and/or the procedure of the blood pressure measurement. This control or regulation unit can be configured such that it opens the named valve and sets the compressor into operation to supply the blood pressure cuff with compressed air. The named unit can furthermore control or regulate the total procedure of the blood pressure measurement including the compressed air action on the blood pressure cuff. The processing and/or the storing and/or the display of the measured data can also be carried out by the control or regulation unit.

The named control or regulation unit is preferably the unit which also controls or regulates the operation of the dialyzer. Provision is preferably thus made that the blood pressure measurement takes place via the software of the dialyzer.

Provision is made in a further embodiment of the invention that at least one pressure sensor is present for detecting the blood pressure, with this sensor forming a component of the dialyzer or being in communication with the dialyzer. The measured pressure value can preferably be displayed at the dialyzer. A pressure sensor already present in the dialyzer can preferably be used as the pressure sensor so that no separate pressure sensor to be provided separately for the blood pressure measurement is required.

The reception of the pressure in the blood pressure cuff can thus take place via a pressure sensor in the dialyzer, with provision preferably being made that a pressure sensor already present in the unit and also required for other pressure measurements is used for this purpose.

Provision is preferably made that the measured blood pressure value is displayed at the display of the dialyzer. It also applies here that a display already present at the unit is preferably used for displaying the blood pressure value or values.

Provision is made in a preferred embodiment of the invention that the dialyzer is configured such that the data acquisition, storage and processing of the data measured by means of the blood pressure cuff takes place in the dialyzer. Accordingly, processors, memories, etc. can be present in the dialyzer which process and/or store the data sensed on the part of the pressure sensor.

Provision is made in a further preferred embodiment of the invention that all the means required for the blood pressure measurement and the processing of the measured data are arranged in the dialyzer, with the exception of the blood pressure cuff. In this embodiment of the invention, only one blood pressure cuff has to be present or to be plugged to the dialyzer. All further components which are required within the framework of the blood pressure measurement such as the pressure sensor or sensors, compressor, control or regulation units, display, memory, processing units for processing the data, etc. are preferably components of the dialyzer. This also applies accordingly to actuation elements such as buttons, switches or the like by means of which the blood pressure measurement can be initiated on the user side.

The fact is generally also covered by the invention that the blood pressure measurement runs fully automatically on the part of the dialyzer, for example in specific predefined time intervals.

Further advantages and particulars of the invention will be explained in more detail with reference to an embodiment shown in the drawing.

The only FIGURE shows a schematic representation of the compressor with valve and blood pressure cuff and the pneumatic system of the peritoneal dialyzer.

Reference numeral 100 designates a compressor of a peritoneal dialyzer.

The pressure side D of the compressor 100 is selectively in communication with the pneumatic system 300 of the peritoneal dialyzer or with the blood pressure cuff 400 depending on the position of the 3/2-way valve 200.

The pneumatic system 300 of the peritoneal dialyzer, for example, comprises pneumatic valves for switching the fluid paths in a disposable cassette, for switching the bleed valves at the hydraulic pump of the peritoneal dialyzer which are required for the degasing of the hydraulic fluid and for the application of compressed air to an air cushion for pressing the disposable set between the drawer and the machine block of the peritoneal dialyzer.

A pressure limitation device is preferably provided which limits the pressure on the pressure side D of the compressor 100 to a maximum value such as to 2 bar.

Reference numeral 500 designates the housing in which the compressor 100 and the valve 200 are located.

The peritoneal dialyzer has software or a control or regulation unit which not only carries out the operation of the peritoneal dialyzer, but rather also the blood pressure measurement. It is also conceivable that the control or regulation for the blood pressure measurement is separate from that of the peritoneal dialyzer.

If a blood pressure measurement is to be carried out, which can take place by actuating a button or the like or in an automated manner by the unit, the valve 200 is moved by an actuator, etc. from its position shown in the FIGURE such that the pressure side of the compressor 100 is in communication with the blood pressure cuff 400 via the line 410 and compressed air can be introduced into the blood pressure cuff 400. In this valve position, the connections 2 and 1 are connected, but not 2 and 3; there is thus no communication between the pressure side of the compressor 100 and the pneumatic system 300 of the peritoneal dialyzer.

After the end of the blood pressure measurement, the air can be let out again via the same line 410.

The procedure of the blood pressure measurement is preferably carried out by a control or regulation unit. This sets the pressure in the blood pressure cuff 400 and takes over the entire further procedure of the blood pressure measurement.

The pressure measurement takes place by means of a pressure sensor of the peritoneal dialyzer. The display of the measured blood pressure takes place at a display of the peritoneal dialyzer. The storage and/or further processing of the blood pressure values can likewise take place in the peritoneal dialyzer.

After the blood pressure measurement, the valve 200 is again moved into its position shown in the FIGURE. The connections 2 and 3, but not the connections 2 and 1, are connected in this valve position; there is thus no communication between the pressure side of the compressor 100 and the blood pressure cuff 400. The resetting of the valve 200 can take place automatically or be initiated by the user.

The valve 200 is preferably biased, e.g. by a spring, into its position shown in the FIGURE so that it is always in the position shown in the FIGURE except for the time duration of the blood pressure measurement. In this position, the compressor is connected at its pressure side via the line 310 to the pneumatic system of the peritoneal dialyzer.

The invention claimed is:

1. A dialyzer comprising
at least one compressor,
at least one blood pressure cuff,
a pneumatic system containing at least one pneumatic consumer in communication with the compressor such that the pneumatic consumer can be acted on by compressed air supplied from the compressor, wherein the dialyzer communicates or can communicate with the at least one blood pressure cuff such that the blood pressure cuff can be supplied with compressed air by the compressor, and
at least one valve located between the compressor and the blood pressure cuff and one or more lines between the compressor and the blood pressure cuff can be closed off or released by said valve, wherein the valve is configured as a multiway valve, which is designed such that either the blood pressure cuff or other consumers are in compressed air communication with the compressor.

2. The dialyzer in accordance with claim 1, wherein the dialyzer has at least one connection to which the blood pressure cuff is or can be releasably connected.

3. The dialyzer in accordance with claim 2, wherein the connection is a plug-in connection.

4. The dialyzer in accordance with claim 1, wherein the dialyzer has a control or regulation unit which is configured such that it controls or regulates the supply of the blood pressure cuff with compressed air and/or the procedure of the blood pressure measurement.

5. The dialyzer in accordance with claim 4, wherein the control or regulation unit is configured such that it controls or regulates the operation of the dialyzer.

6. The dialyzer in accordance with claim 1, further comprising at least one pressure sensor for detecting the blood pressure, with the sensor forming a component of the dialyzer or being in communication with the dialyzer such that the measured pressure value can be displayed at the dialyzer.

7. The dialyzer in accordance with claim 1, wherein the dialyzer is configured such that the data acquisition, storage and processing of the data measured by use of the blood pressure cuff takes place in the dialyzer.

8. The dialyzer in accordance with claim 1, wherein all components required for the blood pressure measurement and for the processing of the measured data are arranged in the dialyzer, with the exception of the blood pressure cuff.

9. The dialyzer according to claim 1, wherein the dialyzer is a peritoneal dialyzer.

10. A dialyzer comprising
at least one compressor, at least one blood pressure cuff, a pneumatic system containing at least one pneumatic consumer in communication with the compressor such that the pneumatic consumer can be acted on by compressed air supplied from the compressor, wherein the dialyzer communicates or can communicate with the at least one blood pressure cuff such that the blood pressure cuff can be supplied with compressed air by the compressor, and at least one valve located between the compressor and the blood pressure cuff and one or more lines between the compressor and the blood pressure cuff can be closed off or released by said valve, wherein the valve is configured as a multiway valve, which is designed such that either the blood pressure cuff or other consumers are in compressed air communication with the compressor, and wherein the multiway valve is a 2-way valve.

\* \* \* \* \*